United States Patent
Cockrem et al.

(10) Patent No.: US 6,641,734 B2
(45) Date of Patent: Nov. 4, 2003

(54) PROCESS FOR PURIFYING AN ORGANIC ACID

(75) Inventors: Michael Charles Milner Cockrem, Madison, WI (US); Istvan Kovacs, Madison, WI (US); Idris Mohamednur, Madison, WI (US); David Heidel, Decatur, IL (US)

(73) Assignee: A. E. Staley Manufacturing Co., Decatur, IL (US)

( * ) Notice: Subject to any disclaimer, the term of this patent is extended or adjusted under 35 U.S.C. 154(b) by 1 day.

(21) Appl. No.: 10/037,664

(22) Filed: Jan. 3, 2002

(65) Prior Publication Data

US 2003/0155298 A1 Aug. 21, 2003

(51) Int. Cl.⁷ .............................................. B01D 11/00
(52) U.S. Cl. ........................ 210/634; 210/669; 435/139; 562/580; 562/589; 562/608
(58) Field of Search ................................. 210/634, 638, 210/639, 749, 663, 669, 680, 691, 692, 774, 806; 562/580, 589, 593, 608; 435/139

(56) References Cited

U.S. PATENT DOCUMENTS 2,568,095 A  *  9/1951  Smith et al.
4,082,788 A  *  4/1978  Mims (List continued on next page.)

FOREIGN PATENT DOCUMENTS

EP          0 049 429 A1     9/1981

OTHER PUBLICATIONS

Tamada et al., "Extraction of Carboxylic Acids with Amine Extractants. 2. Chemical Interactions and Interpretation of Data," *Ind. Eng. Chem. Res.* 29:1327–1333 (1990).

(List continued on next page.)

*Primary Examiner*—Joseph Drodge
(74) *Attorney, Agent, or Firm*—Williams, Morgan and Amerson

(57) ABSTRACT

A process is disclosed for purifying an aqueous feed stream comprising a product organic acid, such as lactic acid, and a strong contaminant, such as pyruvic acid or oxalic acid. The molar concentration of the product organic acid in the feed stream typically is at least 20 times greater than the molar concentration of the strong contaminant. The aqueous feed stream is contacted with a first immiscible basic extractant that has at least a 3-fold greater affinity for the strong contaminant than for the product organic acid. The majority of the strong contaminant and some product organic acid become complexed with the first immiscible basic extractant. The complexed first immiscible basic extractant is separated from the aqueous stream, thereby producing a first effluent stream that comprises product organic acid and that has a greater ratio of molar product organic acid to molar strong contaminant than the aqueous feed stream did. The complexed first immiscible basic extractant is contacted with a displacing acid. The first immiscible basic extractant has a greater affinity for the displacing acid than it does for the strong contaminant or the product organic acid, and as a result, product organic acid and strong contaminant are displaced over a period of time from the complexed first immiscible basic extractant, producing a second effluent stream that comprises a major amount of product organic acid and a third effluent stream that comprises a major amount of strong contaminant.

51 Claims, 3 Drawing Sheets

U.S. PATENT DOCUMENTS

| | | | | |
|---|---|---|---|---|
| 4,275,234 | A | 6/1981 | Baniel et al. | 562/584 |
| 4,291,007 | A | 9/1981 | Baniel | 423/390 |
| 4,334,095 | A | 6/1982 | Baniel | 562/584 |
| 4,994,609 | A | 2/1991 | Baniel et al. | 562/580 |
| 5,068,418 | A | 11/1991 | Kulprathipanja et al. | 562/580 |
| 5,068,419 | A | 11/1991 | Kulprathipanja et al. | 562/580 |
| 5,210,294 | A | 5/1993 | Mantovani et al. | 562/580 |
| 5,231,225 | A | 7/1993 | Baniel et al. | 562/513 |
| 5,426,220 | A | 6/1995 | Baniel et al. | 562/580 |
| 5,574,180 | A | 11/1996 | McQuigg et al. | 558/147 |
| 5,641,406 | A | 6/1997 | Sarhaddar et al. | 210/656 |
| 5,780,276 | A | 7/1998 | Baniel | 435/136 |
| 5,786,185 | A | 7/1998 | Tsao et al. | 435/139 |
| 5,892,109 | A | 4/1999 | Baniel et al. | 562/580 |
| 5,959,144 | A | 9/1999 | Baniel | 562/580 |
| 5,986,133 | A | 11/1999 | Holtzapple et al. | 562/608 |
| 6,001,255 | A | 12/1999 | Eyal et al. | 210/638 |
| 6,087,532 | A | 7/2000 | Baniel et al. | 562/580 |
| 6,111,137 | A | * 8/2000 | Suizi et al. | 562/580 |
| 6,147,259 | A | 11/2000 | Cami et al. | 562/573 |
| 6,280,985 | B1 | 8/2001 | Caboche et al. | 435/139 |
| 6,320,077 | B1 | 11/2001 | Eyal et al. | 562/589 |
| 6,489,508 | B1 | 12/2002 | Van Gansbeghe et al. | 562/589 |
| 6,509,179 | B1 | * 1/2003 | Veldhuis-Stribos et al. | 435/139 |

OTHER PUBLICATIONS

Tamada et al., "Extraction of Carboxylic Acids with Amine Extractants. 3. Effect of Temperature, Water Coextraction, and Process Considerations," *Ind. Eng. Chem. Res.* 29:1333–1338 (1990).

Shevchenko et al., "Extraction of Tartaric, Malic, and Lactic Acids in Tri–n–Butyl Phosphate," *Russian Journal of Inorganic Chemistry* 8:268–271 (1963).

Schuegerl et al., "Recovery of Low–Molecular Weight Compounds from Complex Aqueous Mixtures by Extraction," *International Chemical Journal* 32:29–40 (1992).

Tamada et al., "Extraction of Carboxylic Acids with Amine Extractants. 1. Equilibria and Law of Mass Action Modeling," *Ind. Eng. Chem. Res.* 29:1319–1326 (1990).

Tung et al., "Sorption and Extraction of Lactic and Succinic Acids at pH greater than $pK_{a1}$. 2. Regeneration and Process Considerations," *Ind. Eng. Chem. Res.* 33:3224–3229 (1994).

Tung et al., "Sorption and Extraction of Lactic and Succinic Acids at pH greater than $pK_{a1}$. 1. Factors Governing Equilibria," *Ind. Eng. Chem. Res.* 33:3217–3223 (1994).

San–Martin et al., "Reactive Extraction of Lactic Acid with Alamine 336 in the Presence of Salts and Lactose," *J. Chem. Tech. Biotechnol.* 54:1–6 (1992).

Prochazka et al., "Amine Extraction of Hydrocarboxylic Acids. 2. Comparison of Equilibria for Lactic, Malic, and Citric Acids," *Ind. Eng. Chem Res.* 33:1565–1573 (1994).

Poole et al., "Regeneration of Carboxylic Acid–Amine Extracts by Back–Extraction with an Aqueous Solution of a Volatile Amine," *Ind. Eng. Chem. Res.* 30:923–929 (1991).

Miller et al., "Extraction of Lactic Acid from a Calcium Lactate Solution Using Amine–Containing Solvents and Carbon Dioxide Gas," *Ind. Eng. Chem. Res.* 35:1156–1162 (1996).

Kulprathipanja et al., "Adsorptive Separation of Organic Acids by the Sorbex Process," *Separation Technology*, Vansant ed., Elsevier Science B.V. (1994).

Juang et al., "Comparison of Extraction Equilibria of Succinic and Tartaric Acids from Aqueous Solutions with Tri–n–octylamine," *Ind. Eng. Chem. Res.* 35:1944–1950 (1996).

Kertes et al., "Extraction Chemistry of Fermentation Product Carboxylic Acids," *Biotechnology and Bioengineering* 28:269–282 (1986).

King, "Amine–Based Systems for Carboxylic Acid Recovery," *Chemtech* May:285–291 (1992).

Chanda et al., "Sorption of Phenolics and Carboxylic Acids on Polybenzimidazole," *Reactive Polymers* 4:39–48 (1985).

Evangelista et al., "Recovery of Lactic Acid by Sorption: Resin Evaluation," *Applied Biochemistry and Biotechnology* 45:131–145 (1994).

* cited by examiner

PROCESS FOR PURIFYING AN ORGANIC ACID

BACKGROUND OF THE INVENTION

The present invention relates generally to processes for producing organic acids, such as lactic acid.

Lactic acid has a number of commercial uses, for example in food manufacturing, pharmaceuticals, plastics, textiles, and as a starting material in various chemical processes. In addition, it is used in the manufacture of polylactic acid, a degradable plastic.

Although organic acids can be prepared by chemical synthesis, production by fermentation is generally less expensive. It is well known to produce lactic acid by fermentation using microorganisms such as *Lactobacillus delbrueckii*. The broth that results from fermentation contains unfermented sugars, carbohydrates, amino acids, proteins, and salts, as well as organic acids, such as lactic acid. Typically, the organic acid is recovered from the fermentation broth and undergoes further purification before it is used. Purified organic acids recovered from fermentation broths can comprise small amounts of impurities, such as strong acids or certain unknown compounds. Some of these impurities can cause an undesirable color or can interfere with downstream processing of the organic acid. For example, lactic acid as it is sold commercially typically comprises small amounts of impurities such as pyruvic acid and oxalic acid. Even though present in relatively small amounts, such impurities can have negative effects on polymers produced from the lactic acid. For example, when lactic acid is polymerized to produce polylactic acid (PLA), the presence of even small amounts of pyruvic acid can cause the polymer to have an undesirable yellow color. However, it is difficult to further purify lactic acid that contains only a small fraction of pyruvic acid in the first instance.

Thus, there is a need for improved processes for the production and recovery of relatively pure organic acids, particularly lactic acid.

SUMMARY OF THE INVENTION

One aspect of the present invention is a process for purifying an aqueous feed stream that comprises a desired product organic acid and at least one strong contaminant. In certain embodiments, the aqueous feed stream can comprise a fermentation broth or can be obtained from a fermentation broth. (Whenever an acid is referenced herein, either as the desired product or as a contaminant, it should be understood that some or all of the acid may be present in the form of salts.) The molar concentration of the product organic acid in the feed stream can be at least 10 times greater than the molar concentration of the strong contaminant, and more preferably the molar concentration of the product organic acid to the strong contaminant is at least 20. In certain embodiments the molar concentration of the product organic acid to the strong contaminant is at least 90, in certain embodiments it is at least 500 and in certain embodiments it is at least 1000. The aqueous feed stream is contacted with a first immiscible basic extractant that has a selectivity, under the existing process conditions (including the combination of acids, solvents, etc., that are present) for the strong contaminant relative to the product organic acid that is greater than 3. The selectivity, which is further defined below, is preferably greater than 15, more preferably greater than about 25, most preferably greater than about 100. Preferably the selectivity is greater than the ratio of product organic acid to strong contaminant in the feed.

The contacting step in which the aqueous feed stream is contacted with a first immiscible basic extractant is preferably performed with sufficient equilibrium or near equilibrium stages, and with sufficient quantity of the first immiscible basic extractant (such as a solid amine ion exchanger or liquid amine extractant) to remove the majority of the strong contaminant. In certain embodiments the first immiscible basic extractant has previously been used to treat a solution comprising the product organic acid and at least one weak contaminant (e.g., it is recycled).

As a result, the majority of the strong contaminant and less than about 33 wt % of the product organic acid become complexed with the first immiscible basic extractant. "Majority" as used herein means more than 50% by weight of the substance, in this case the strong contaminant, that is present. In other words, more than 50% by weight of the strong contaminant present in the feed complexes with the extractant. The complexed first immiscible basic extractant is separated from the aqueous stream, thereby producing a first effluent stream that comprises product organic acid and that has a greater ratio of product organic acid to strong contaminant than the aqueous feed stream did. The complexed first immiscible basic extractant is contacted with a displacing acid. The first immiscible basic extractant has a greater affinity for the displacing acid than it does for the strong contaminant or the product organic acid, and as a result, product organic acid and strong contaminant are displaced over a period of time from the complexed first immiscible basic extractant. This produces a second effluent stream that comprises a major amount of product organic acid (i.e., more than 50% by weight of the solids dissolved or suspended in the stream are the product organic acid) and a third effluent stream that comprises a major amount of strong contaminant. Preferably, the total amount of product organic acid present in the first effluent stream and in the second effluent stream is at least about 90% by weight of the product organic acid that was present in the feed stream. More preferably, at least about 98% by weight of the product organic acid is recovered in those streams.

In many embodiments of the process, the strong contaminant comprises an organic acid that has a $pK_a$ that is lower than the $pK_a$ of the product organic acid. If the desired product organic acid is lactic acid, the strong contaminant preferably has a $pK_a$ less than about 3.46. In certain specific embodiments of the process involving a basic extractant that is a solid ion exchange resin, the strong contaminant is selected from the group consisting of pyruvic acid, oxalic acid, citraconic acid, citric acid, and mixtures thereof.

In other embodiments, the strong contaminant can be a weaker acid (e.g., higher $pK_a$) than the desired organic acid product, but can have greater hydrophobic and/or hydrogen bonding character than the product. The strong contaminant is selectively removed relative to the organic acid of interest by an immiscible basic extractant comprising a solvent or a solvent mixture, for example an amine mixture comprising 1 M trilaurylamine and 1 M dodecanol with dodecane as a diluent.

When the immiscible basic extractant comprises a solvent mixture, preferably the organic acid of interest has somewhat hydrophobic or strong hydrogen bonding characteristics, and the strong contaminant must either (1) be of similar H-bonding and/or hydrophobic character and lower $pK_a$ than the acid of interest (acidic low $pK_a$ species) or (2) have a sufficiently stronger H-bonding and/or hydrophobic character so that the strong contaminant can still be removed despite its having a higher relative $pK_a$. Thus, if the strong contaminant has a lower $pK_a$ than the organic acid product, a solid ion exchange resin can be used as an extractant to remove the strong contaminant. For example, if the organic acid to be recovered is lactic acid, strong contaminants that can be removed by methods of the present invention involving ion exchange resins include HCl, $H_2SO_4$, pyruvic acid and oxalic acid, among others. Acetic acid and butyric acid do not, however, have significantly lower $pK_a$ values than lactic acid, and they are not as readily removed by ion exchange resins. However strong contaminants having either low $pK_a$ or high hydrophobicity/hydrogen bonding characteristics relative to the organic acid product, can be removed using extractants that are solvents or a solvent mixture. For example, pyruvic acid, $H_2SO_4$, and butyric acid can be removed from an aqueous feed stream comprising lactic acid with use of an amine solvent extractant of the present invention. Although the first immiscible basic extractant can take various forms, one that is preferred is a weak base ion exchange resin. Preferably the weak base ion exchange resin comprises a tertiary amine moiety. One of the advantages of many embodiments of this process is the ability to further purify a stream that already contains a very low percentage of impurities. For example, in one embodiment, the molar concentration of lactic acid, e.g., the product organic acid, in the feed stream is at least 20 times greater than the molar concentration of the strong contaminant in the feed stream, and the selectivity is greater than about 25. In another embodiment, the molar concentration of the lactic acid, e.g., the product organic acid, in the feed stream is at least 300 times greater than the molar concentration of the strong contaminant in the feed stream, and the selectivity is greater than about 500.

In one embodiment of the process, the feed stream, the first effluent stream, and the second effluent stream further comprise a weak contaminant. For example, where the product organic acid is lactic acid, the weak contaminant can be an organic acid having a $pK_a$ greater than about 4.26, such as propionic acid, butyric acid, malonic acid, succinic acid, or mixtures thereof. In this situation, the process can further comprise the steps of combining the first effluent stream and the second effluent stream to form a combined product organic acid stream, and then contacting the combined product organic acid stream with a second immiscible basic extractant. The majority of the product organic acid becomes complexed with the second immiscible basic extractant. Preferably, at least 90% by weight of the product acid becomes complexed, more preferably at least 95%. The complexed second immiscible basic extractant can then be separated from the stream, thereby producing a fourth effluent stream that comprises the majority of the weak contaminant that was present in the combined product organic acid stream. Preferably the second immiscible basic extractant comprises a weak or strong base ion exchange resin.

Optionally, this embodiment of the process can further comprise contacting the fourth effluent stream with a third immiscible basic extractant that has a greater affinity for the product organic acid than for the weak contaminant, whereby the majority of the product organic acid that is present in the fourth effluent stream becomes complexed with the third immiscible basic extractant. The complexed third immiscible basic extractant can then be separated from the stream, thereby producing a fifth effluent that comprises the majority of the weak contaminant that was present in the combined product organic acid stream. Then the complexed second immiscible basic extractant and the complexed third immiscible basic extractant can be contacted with one or more displacing acids, thereby displacing product organic acid therefrom in one or more additional effluent streams.

In another variation of the process, the third effluent stream is contacted with an additional immiscible basic extractant that has a greater affinity for the strong contaminant than for the product organic acid. As a result, the majority of the strong contaminant present in the third effluent stream becomes complexed with the additional immiscible basic extractant. The complexed additional immiscible basic extractant is separated from the remaining stream, thereby producing an additional effluent that comprises the majority of the product organic acid that was present in the third effluent.

One particularly preferred embodiment of the invention is a process for purifying lactic acid. The embodiment involves providing an aqueous feed stream comprising lactic acid (defined herein to include any salts thereof) and at least one strong contaminant acid having a $pK_a$ less than about 3.46. The molar concentration of lactic acid in the feed stream is at least 20 times greater than the molar concentration of strong contaminant acid. The aqueous feed stream is contacted with a first basic ion exchanger that has a greater affinity for the strong contaminant acid than for lactic acid, such that the majority of the strong contaminant acid and some lactic acid become complexed with the first basic ion exchanger. The complexed first basic ion exchanger is separated from the aqueous stream, producing a first effluent stream that comprises lactic acid and that has a greater ratio of lactic acid to strong contaminant acid than the aqueous feed stream did. The complexed first basic ion exchanger is contacted with a displacing acid, such as HCl, $H_2SO_4$, or $H_3PO_4$, and the first basic ion exchanger has a greater affinity for the displacing acid than it does for the strong contaminant acid or lactic acid. Lactic acid and strong contaminant acid are displaced over a period of time from the complexed first basic ion exchanger, producing a second effluent stream that comprises a major amount of lactic acid, and a third effluent stream that comprises a major amount of strong contaminant acid.

In some embodiments of this process, the strong contaminant acid is selected from the group consisting of pyruvic acid, oxalic acid, citraconic acid, citric acid, and mixtures thereof. In certain embodiments of the process, the molar concentration of lactic acid in the feed stream is at least 100 times greater than the molar concentration of the strong contaminant acid in the feed stream and the selectivity is greater than about 250. In certain embodiments, the ratio is at least 300 and the selectivity is greater than about 500.

Preferably, the first basic ion exchanger has an affinity for the displacing acid that is at least 10 times greater than its affinity for pyruvic acid.

Preferably, the first effluent stream and the second effluent stream collectively have a ratio of lactic acid to strong contaminant that is greater than 300. More preferably, they collectively have a ratio of molar lactic acid to molar strong contaminant that is greater than about 1,000. In some embodiments of the process, at least 90%, and more preferably 98% by weight of the lactic acid present in the feed stream is recovered in the first effluent stream and the second effluent stream.

In a particular embodiment of the process, the aqueous feed stream comprises no more than about 0.15 moles of cations selected from the group consisting of Ca, Mg, Na, Fe, Zn, Zr, and Li, per mole of lactic acid; no more than about 0.05 moles of anions selected from the group consisting of Cl, $SO_4$, $PO_4$, and $NO_3$, per mole of lactic acid; nor more than about 0.03 mole of strong acid contaminants selected from the group consisting of pyruvic acid, oxalic acid, citraconic acid, and citric acid, per mole of lactic acid; and no more than about 0.02 mole of weak acid contaminants selected from the group consisting of propionic acid, butyric acid, malonic acid, and succinic acid, per mole of lactic acid.

Another aspect of the invention is a process for purifying lactic acid involving providing an aqueous fermentation broth comprising lactic acid (defined herein to include any salts thereof) and pyruvic acid (also defined herein to include any salts thereof). The molar concentration of the lactic acid is at least 20 times greater than the molar concentration of pyruvic acid in the aqueous fermentation broth. Cells are removed from the broth to form an aqueous feed stream. Any method known in the art for removing cells can be used (e.g., centrifugation or filtration, among others). The aqueous feed stream is contacted with means for complexing pyruvic acid, and the means has a greater affinity for pyruvic acid than for lactic acid, so that the majority of the pyruvic acid and some lactic acid form complexes therewith. The complexes are separated from the aqueous stream, thereby producing a first effluent stream that comprises lactic acid and that has a greater ratio of lactic acid to pyruvic acid than the aqueous feed stream did. The complexes are contacted with means for displacing lactic acid and pyruvic acid therefrom, thereby producing a second effluent stream that comprises a major amount of lactic acid and a third effluent stream that comprises a major amount of pyruvic acid.

In certain embodiments the first immiscible basic extractant is a solid basic extractant, and the aqueous feed stream is contacted with the first immiscible basic extractant in a packed bed. Preferably in embodiments involving a packed bed, the ratio of molar concentration of product organic acid to molar concentration of strong contaminant in the second effluent stream is within about 10% of the selectivity.

In other embodiments, the first immiscible basic extractant is a liquid basic extractant, and the aqueous feed stream is contacted with the first immiscible basic extractant in a multistage process. Preferably the ratio of product organic acid to strong contaminant is within about 10% of the selectivity.

Furthermore, in certain embodiments the aqueous feed stream comprises more than one strong contaminant, and at least one of the strong contaminants is a displacing acid.

Certain embodiments are directed to a process involving an aqueous feed stream that comprises a desired product organic acid, at least one strong contaminant, and a weak contaminant. The first effluent stream also comprises the weak contaminant, and the first effluent stream is processed by at least one of extraction or distillation (by methods known in the art), whereby at least two fractions are produced, a purified product organic acid fraction comprising between about 90% and 99.5% by weight of the product organic acid that was present in the feed stream, and a weak contaminant fraction comprising product organic acid and weak contaminant. The ratio of molar concentration of product organic acid to molar concentration of weak contaminant in the weak contaminant fraction is less than the ratio of molar concentration of product organic acid to molar concentration of weak contaminant in the feed stream. The weak contaminant fraction is contacted with a third immiscible basic extractant that has a selectivity for the product organic acid relative to the weak contaminant that is greater than about 3, and the majority of the product organic acid and less than about 33 wt % of the weak contaminant become complexed with the third immiscible basic extractant. The complexed third immiscible basic extractant is separated from the aqueous stream, to produce an effluent stream that comprises weak contaminant. The effluent stream that comprises weak contaminant has a greater ratio of weak contaminant to product organic acid than the aqueous feed stream did. The complexed third immiscible basic extractant is contacted with a displacing acid, and the third immiscible basic extractant has a greater affinity for the displacing acid than it does for the product organic acid or the weak contaminant. The displacing acid is present in sufficient amount to cause product organic acid and weak contaminant to be displaced over a period of time from the complexed third immiscible basic extractant to produce a weak contaminant effluent stream that comprises a major amount of weak contaminant and a product organic acid stream that comprises a major amount of the product organic acid. Preferably the purified product organic acid fraction comprises between about 95% by weight and 99.5% by weight of the product organic acid that was present in the feed stream.

Certain embodiments are directed to a process for purifying an organic acid that comprises providing an aqueous feed stream comprising a product organic acid and one strong contaminant. The molar concentration of the product organic acid is at least 20 times greater than the molar concentration of the strong contaminant. The aqueous feed stream is contacted with a first immiscible basic extractant that has a selectivity for the strong contaminant relative to the product organic acid that is greater than about 3. The majority of the strong contaminant and less than about 33 wt % of the product organic acid become complexed with the first immiscible basic extractant. The complexed first immiscible basic extractant is separated from the aqueous stream, thereby producing a first effluent stream that comprises product organic acid and that has a greater ratio of product organic acid to strong contaminant than the aqueous feed stream did. The complexed first immiscible basic extractant is exposed to at least one of (1) a change in temperature, (2) a change in solvent concentration, or (3) a change in displacing agent concentration. The exposure causes product organic acid and strong contaminant to be displaced over a period of time from the complexed first immiscible basic extractant, thereby producing a second effluent stream that comprises a major amount of product organic acid and a third effluent stream that comprises a major amount of strong contaminant. The change in solvent concentration can be achieved using methods known in the art, such as evaporation solvents present in the aqueous feed stream. Furthermore combinations of temperature change, solvent change, and/or displacing acid or base concentration can be used to obtain selective release of desired product or of the impurities from the complexed first immiscible basic extraction. The displacing agent can be either a displacing acid as discussed above, or a displacing base. A base, such as NaOH, can be used as a displacing agent, and the displaced material can then be treated using methods known in the art to recovered the desired product organic acid.

DESCRIPTION OF ILLUSTRATIVE EMBODIMENTS

The process of the present invention can be used to recover and purify a variety of organic acids. The process is especially well suited for recovery and purification of a monocarboxylic, dicarboxylic, or tricarboxylic acid having from 2 to 8 carbon atoms. Preferably, the organic acid is a hydroxy organic acid (or a mixture of two or more such acids). The hydroxy organic acid can be an alpha, beta, delta, gamma, or epsilon hydroxy acid. Most preferably, the organic acid is lactic acid.

The process of the present invention can recover purified organic acid from a fermentation broth. However, the process is also suitable for use in purifying organic acids from other sources, such as lactic acid of commerce. "88% lactic acid" and "lactic acid of commerce" refer to a typical commercially available lactic acid, which is actually a mixture of monomeric lactic acid, linear dimer lactic acid or lactoyl lactic acid, short chain lactic acid oligomers, water, a small quantity of cyclic dimer lactic acid or lactide, and small amounts of impurities. When commercial lactic acid is diluted in a large excess of water, the dimers and oligomers slowly hydrolyze or convert to the monomeric form of lactic acid. When concentrated lactic acid is diluted with water to a 50 wt % concentration, dimers and oligomers initially present will slowly hydrolyze to a mixture that is largely monomeric lactic acid, but which can still contain about 3 to 4 wt % dimer lactic acid, and trace amounts of higher oligomers.

Figure 1:
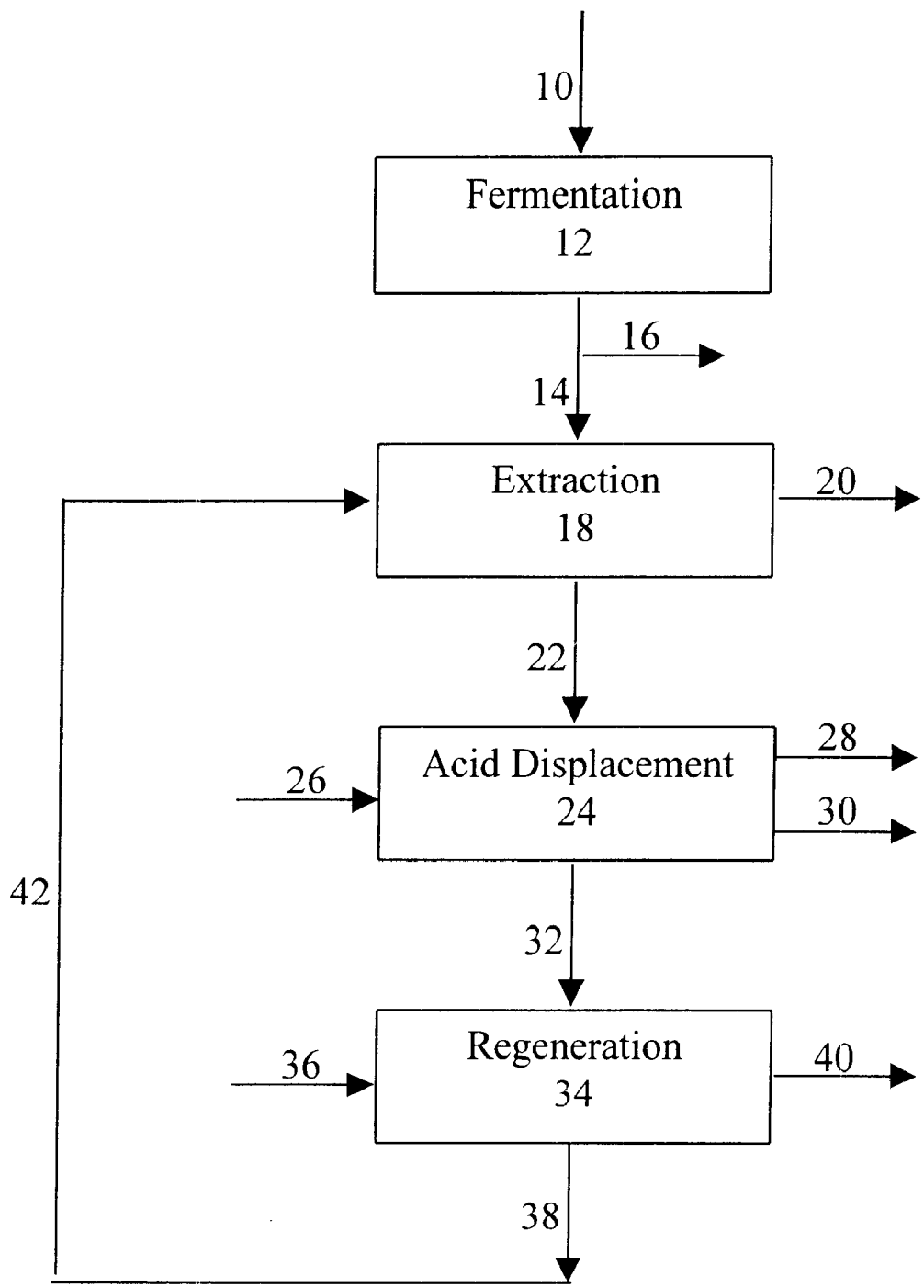
FIG. 1 is a process flow diagram of one embodiment of the present invention.

FIG. 1 shows an embodiment of the process for recovering lactic acid from a fermentation broth. A seed train 10 is fed to a fermentation vessel 12 that contains fermentation medium. The fermentation produces an aqueous broth that comprises the desired organic acid, in this case lactic acid. (Whenever an organic acid is referred to in this patent, including in the claims, it should be understood that some or all of the acid can be present in the form of salts. For the sake of brevity, any reference to the acid herein covers either form (free acid or salt), or a mixture of both.) The broth also contains one or more strong contaminants, in this case pyruvic acid, as well as unfermented sugars and other impurities. In some embodiments of the process, the ratio of the desired product acid (e.g., lactic acid) in molar concentration to molar concentration of the strong impurity (e.g., pyruvic acid) is greater than about 300. In certain embodiments the ratio of the desired product acid (e.g., lactic acid) in molar concentration to molar concentration of the strong impurity (e.g., pyruvic acid) is greater than about 500, and in certain embodiments its greater than 1000.

A "strong contaminant" as used herein means a chemical species, such as an organic acid, for which the immiscible basic extractant selected for use has at least a 3 fold greater selectivity or affinity than for the product of interest.

For embodiments of the present invention in which a solid immiscible basic extractant comprising an anion exchange resin is used, a strong contaminant that is to be removed from an organic acid aqueous feed stream can have a lower $pK_a$ value than that of the organic acid that is to be recovered from the feed stream.

For embodiments of the present invention involving liquid immiscible basic extractants comprising a solvent, a strong contaminant either (a) has a lower $pK_a$ value than that of the organic acid that is to be recovered from the feed stream, or (b) the strong contaminant has a similar or higher $pK_a$ value than the organic acid of interest, but is more hydrophobic or has more hydrogen bonding groups or both.

For example, for the case of solid ion exchange extractants, oxalic acid ($pK_a$=1.27) and pyruvic acid ($pK_a$=2.48) are strong contaminants in a solution of lactic acid ($pK_a$=3.86). Examples of other strong contaminants that can be present in a lactic acid feed stream include citraconic acid, citric acid, and other organic acids with $pK_a$ values less than about 3.46. Weak contaminants that are not removed by the solid ion exchange extractant can include non-acidic species such as glucose, and weak acids such as acetic acid, succinic acid, and butyric acid.

As an example for the case of liquid amine based immiscible extractants at 20–30 deg C. used to recover lactic acid from a solution, strong contaminants can include both strong acids, such as above, as well as hydrophobic weak acids. Examples of hydrophobic weak acids that can be removed by liquid immiscible extractants are n-butyric acid, iso-butyric acid, and cyclic weak aromatic acids, such as benzoic acid, among others.

In some embodiments of the process, the feed may comprise one or more strong contaminants of unknown chemical composition. For example, certain lactic acids sold commercially comprise contaminants of unknown chemical composition that have apparent $pK_a$ values less than about 3.46. Using the present invention, a feed stream comprising such a lactic acid can be purified to have a lower concentration of some of these unknown contaminants. The broth 14 is withdrawn from the fermentation vessel 12. Cells in the broth can be separated, for example by filtration or centrifugation, and removed as a waste stream 16. Optionally, the broth can be further purified by removing strong anions and/or cations. Strong anions such as chloride, sulfate, phosphate, and nitrate can be selectively removed from neutral or acidic pH streams containing organic acid at high selectivity. Strong cations that can be removed include Ca, Mg, K, Na, Fe, Zn, Zr, and Li cations, among others. For example, the fermentation broth can be contacted with a cation exchanger (e.g., strongly acidic cation exchanger), an anion exchanger (e.g., weakly basic anion exchanger), or both sequentially.

The broth 14 is then contacted with a first immiscible basic extractant in step 18. Preferably, this is done using counter-current flow. A mixer-settler apparatus can be used, among other possibilities. This extractant is "immiscible" in that it does not mix with the broth, but the extractant may or may not be liquid. For example, the extractant can comprise an amine compound that has the ability to form complexes with one or more of the organic acids present. In particular, this first extractant should have an affinity for the strong contaminant (pyruvic acid) that is greater than its affinity for the desired product (lactic acid). "Affinity" as used herein means the tendency to complex with another species, such as lactic acid or pyruvic acid, under the existing process conditions, including the particular combination of acids, solvents, and other ingredients that are present. Equal affinity would mean that when contacted with a solution of 50% lactic acid and 50% pyruvic acid, the extractant would complex with equal amounts of the two acids. Because the feed solutions in the present invention will often comprise a high ratio of lactic acid to pyruvic acid, the extractant's affinity for the contaminant (pyruvic acid) should be much greater than its affinity for lactic acid. Preferably, the extractant's affinity for pyruvic acid is at least about 20 times greater than its affinity for lactic acid.

The amine liquid extractant can comprise a primary, secondary or tertiary amine. In certain embodiments, the amine is an alkylamine in which the aggregate number of carbon atoms is from about 4 to 36. Specific examples include n-butylamine, tri-n-butylamine, octylamine, tri-n-octylamine, di-decylamine, dodecylamine, and tri-dodecylamine (also called trilaurylamine), among others. The amine should be immiscible with the aqueous feed solution such that two phases are formed. A liquid extractant of the present invention can optionally also comprise a diluent and/or an enhancer. A diluent can be used as a component of the basic immiscible extractant to lower its viscosity, or to increase the selectivity of the extractant against other unwanted species, among other reasons. Suitable diluents include, for example, pure or mixed aromatic or aliphatic hydrocarbons, such as xylene, toluene, decane, dodecane, kerosene, and mixtures thereof. "Enhancer" refers to a chemical species that acts to enhance the performance of the basic immiscible extractant. The enhancer can strengthen the basic immiscible extractant:strong contaminant complex or immiscible extractant:organic acid complex and/or help solubilize the complex. Examples of suitable enhancers include polar species selected from alcohols, diols, ketones, diketones, fatty acids, chlorinated species, and other species known in the art.

Alternatively, the first basic extractant can comprise a basic ion exchange resin. The ion exchange resin should have a greater affinity for the strong contaminant than it does for the desired product, as described above. Suitable ion exchange resins include pyridine resins, imidazole resins, and tertiary amine resins, among others. One specific example is Ionac A365 (Sybron Chemicals, Birmingham, N.J.). Strong base and weak base ion exchangers can also be used. It is preferred that the amount of the first extractant used in the process be sufficient to create an overall complexing capacity that is greater than theoretically needed to complex with all of the pyruvic acid or other strong contaminant present. In this way, despite the fact that some lactic acid will be complexed as well, the fraction of pyruvic acid complexed can be maximized.

The first basic extractant, which has a greater affinity for pyruvic acid than for lactic acid, forms complexes with the majority of the pyruvic acid that is present in the broth. Due to the relatively large concentration of lactic acid in the broth, the extractant also forms some complexes with lactic acid, despite its lower affinity for that acid. Thus, with the majority of the pyruvic acid removed, a first effluent stream 20 is produced that has a higher ratio of lactic acid to pyruvic acid (M lactic acid:M pyruvic acid) than the original broth 14.

The first basic extractant can then be separated from most of the pyruvic and lactic acid in the complex by an acid displacement step 24. A stream 26 comprising an aqueous solution of a displacing acid, such as HCl, $H_3PO_4$, oxalic acid, $H_2SO_4$ or trifluoroacetic acid, is contacted with the first extractant, which at this point is still complexed with pyruvic and lactic acid. Preferably, the displacing acid has a $pK_a$ of about −2 to 1.8. The displacing acid can also be present in a mixture with other organic acids and species, such as a mixture of HCl, $H_2SO_4$, lactic acid and acetic acid. Preferably the concentration of the displacing acid is from between about 1 and 40%, more preferably from 2 to 5% for $H_2SO_4$ and from 20 to 30% for mixtures containing various acids. In the case of mixtures of various acids, only the acids having a $pK_a$ of about −2 to 1.8 present in that mixture will act as displacing acids.

Because the extractant (i.e., ion exchanger) has a greater affinity for the displacing acid than for either lactic acid or pyruvic acid, the latter two acids are displaced from the complexation sites. Since the extractant has a lower affinity for lactic acid than for the other two acids, lactic acid tends to be displaced first, and is removed as a lactic acid rich-second effluent stream 28. This lactic acid-rich stream optionally can be combined with the first effluent stream 20 to form a combined lactic acid product stream. Preferably, this stream comprises at least about 98% by weight of the lactic acid that was present in the feed, and less than about 20 ppm each of pyruvic acid and oxalic acid, more preferably less than about 10 ppm, most preferably less than about 2 ppm.

After the majority of the lactic acid has been displaced, the pyruvic acid starts to be displaced in greater quantities. This therefore generates a pyruvic acid-rich third effluent stream 30, which optionally can be purified for use in processes that require that particular acid.

A stream 32 is generated that comprises the first extractant, which is now complexed with the displacing acid. This stream 32 is subjected to a basic regeneration step 34, in which a stream 36 comprising a base such as 5% aqueous solution of NaOH is contacted with the complexed first extractant. The base displaces the displacing acid from the extractant, thus creating a stream 38 of regenerated first extractant, which can be recycled 42 for use in the step 18. This operation also produces a stream 40 comprising regenerating acid, which optionally can be recycled for use in stream 26.

Other methods of regenerating the first extractant could be used as well.

Figure 2:
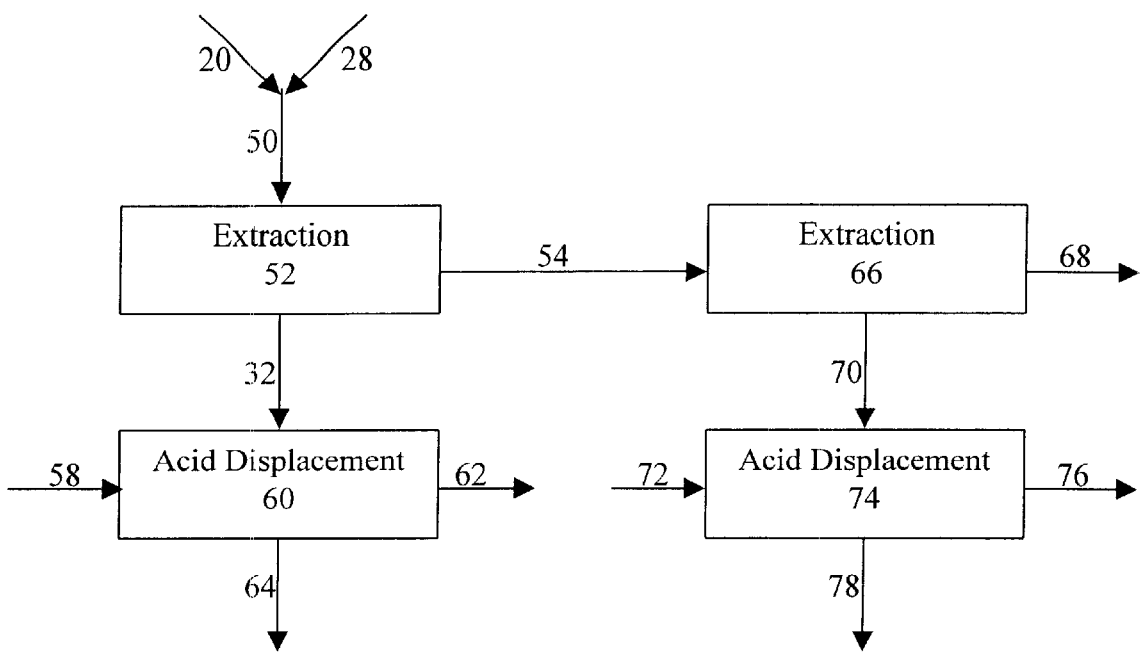
FIG. 2 is a process flow diagram of another embodiment of the present invention, comprising steps that can be performed in addition to those shown in FIG. 1.

FIG. 2 shows optional downstream process steps that are well suited for use when the original feed to the process comprises a weak contaminant as well as a strong contaminant.

A "weak contaminant" as that term is used herein relates to embodiments of the present invention involving solid amine extractants, and means a chemical compound that has a $pK_a$ value greater than that of the organic acid that is to be recovered.

A "weak contaminant" as that term is used herein for the situation of liquid amine mixtures means a chemical compound that has a $pK_a$ value greater than that of the organic acid that is to be recovered and typically is not highly hydrophobic nor prone to forming strong hydrogen bonds with various components of the liquid amine mixture.

For example, for solid based amines, acetic acid, which has a $pK_a$ value of 4.76, can be a weak contaminant present in a feed stream comprising lactic acid. Other examples of weak contaminants that commonly are present in a lactic acid feed stream, especially one obtained from a fermentation broth, include propionic acid, butyric acid, acetic acid, malonic acid, succinic acid, and other organic acids having a $pK_a$ greater than about 4.26.

For example, for liquid extractants that are mixtures comprising immiscible amines, acetic acid, which has a $pK_a$ value of 4.76, can be a weak contaminant present in a feed stream comprising lactic acid. However, in this case butyric acid is not a weak contaminant, relative to lactic acid, in typical solvents, due to its hydrophobic character.

In FIG. 2, the first effluent stream 20 and the second effluent stream 28 are combined to form a combined lactic acid product stream 50. The combined product stream is then contacted in step 52 with a second immiscible basic extractant. The second immiscible basic extractant can be, for example, a weak base ion exchange resin, such as Amberlite IR35, comprising a tertiary amine moiety. This second extractant preferably has a greater affinity for lactic acid than for acetic acid . In addition, the amount of this extractant present should be more than sufficient to complex with essentially all of the lactic acid present in the steam. Therefore, the second extractant forms complexes primarily with lactic acid, and to a much smaller degree with acetic acid. The complexes are separated from the remaining liquid as part of stream 56, thus leaving a fourth effluent stream 54.

The fourth effluent 54 is contacted with a third immiscible basic extractant, which is preferably a basic ion exchange resin. Suitable resins include Amberlite IR 35. This third extractant preferably has a greater affinity for lactic acid than for pyruvic acid. Therefore, most of the lactic acid in the fourth effluent complexes with the ion exchanger, and the complexes are removed in stream 70. A fifth effluent stream 68 is generated which is rich in the weak contaminant.

The streams 56 and 70 comprise complexes of the second and third extractants with primarily lactic acid. The lactic acid can therefore be recovered by contacting these complexes with streams 58 and 72 of displacing acid. Since the second and third extractants have greater affinity for the displacing acid than for lactic acid, the latter is displaced into additional effluent streams 62 and 76, from which it can be recovered. These streams 62 and 76 preferably comprise more than about 90% by weight of the lactic acid that was present in the combined stream 50, more preferably at least about 95%.

The streams 64 and 78 comprise the ion exchangers complexed with displacing acid, which can subsequently be regenerated by contact with a base (not shown in FIG. 2), and then can be recycled for further use in the process.

Figure 3:
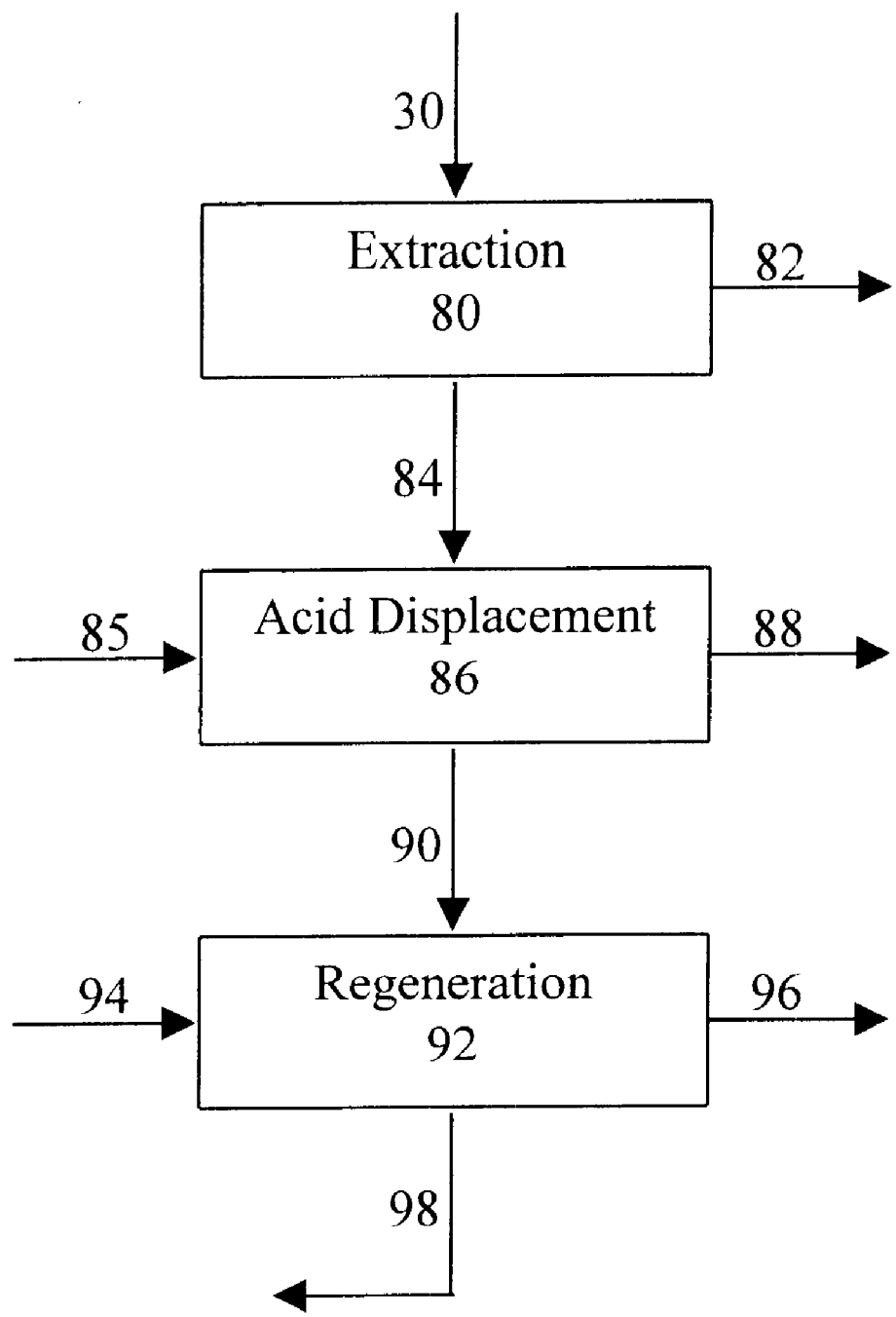
FIG. 3 is a process flow diagram of yet another embodiment of the present invention, comprising steps that can be performed in addition to those shown in FIG. 1.

FIG. 3 shows another set of optional steps that can be performed in addition to those shown in FIG. 1. This variation of the process is especially useful when the ratio of lactic acid to pyruvic acid (Molar lactic acid:Molar pyruvic acid) in the original feed is greater than about 300. In this variation of the process, the third effluent stream 30, which is rich in pyruvic acid, is contacted with an additional immiscible basic extractant in the step 80. This extractant has a greater affinity for the pyruvic acid than for lactic acid, and preferably is an ion exchange resin such as Amberlite IR-35. Therefore, the extractant complexes primarily with pyruvic acid, and these complexes are removed in stream 84. An additional lactic-acid rich effluent stream 82 is generated, from which lactic acid can be recovered.

The stream 84 comprising complexes of ion exchanger and primarily pyruvic acid is then contacted in step 86 with a stream 85 comprising a displacing acid, such as HCl, 4% solution in water. The extractant has a greater affinity for the displacing acid than for the pyruvic acid, and therefore the latter is displaced as the former complexes with the extracted. The pyruvic acid is removed in effluent stream 88, while a stream 90 comprising the complexes of the displacing acid proceeds to a regeneration step 92, in which the complexes are treated with a base stream 94. The result is a regenerated resin stream 98 that can be recycled for further use in the process, and an effluent stream 96 that comprises the displacing acid, which can also be recycled.

The process embodiments described above achieve high selectivity, and thus are highly effective in removing contaminants from an organic acid solution or suspension, even if it is relatively pure in the first instance. This ability to remove selectively an impurity that is present at a low concentration is a major advantage of many embodiments of the present invention. "Selectivity" as used herein refers to the apparent or effective selectivity of the extractant under the process conditions, including the concentrations of desired product acid, contaminants, solvents, and other ingredients to which the extractant is exposed, which ingredients may be present in more than one liquid phase. The selectivity (S) often is slightly less than the theoretical selectivity due to contacting constraints, among other reasons. Theoretical selectivity can be expressed in terms of the following equation:

$$\text{theoretical selectivity} = \frac{\dfrac{\text{amount of strong contaminant complexed with immiscible basic extractant}}{\text{amount of organic acid complexed with immiscible basic extractant}}}{\dfrac{\text{amount of strong contaminant in effluent stream}}{\text{amount of organic acid in effluent stream}}}$$

The amount referred to in the equation can be any quantitative measurement such as the area of a gas chromatography peak or a HPLC peak, moles, and grams, among others. The selectivity will be greater than about 1, and preferably much greater than 1. Preferably, where the desired product is lactic acid, the selectivity is at least about 10. Preferably, the selectivity is at least 80% of the theoretical selectivity. More preferably the selectivity is at least about 90% to 95% of the theoretical selectivity, and most preferably at least about 99% of the theoretical selectivity.

Preferably, the ratio of the molar concentration of the organic acid to the molar concentration of the strong contaminant in the feed stream is at least about equal to the selectivity for the strong contaminant. If the feed stream comprises lactic acid, preferably the ratio of M lactic acid to M pyruvic acid (the strong contaminant) is greater than about 18. In certain embodiments of the process, the ratio of organic acid to strong contaminant (M organic acid:Molar strong contaminant) is greater than the selectivity (S) for the strong contaminant and less than the square of the same selectivity ($S^2$). In still other embodiments of the process, the ratio in the feed is even greater than $S^2$.

FIGS. 1–3 illustrate certain specific combinations of steps that can be used, but those skilled in the art will recognize that there would be many ways to implement the present invention. For example, the process can be operated in a batch, continuous, or semi-continuous manner. Certain embodiments of the invention can be further understood from the following examples.

EXAMPLE 1

Selectivity of Resin IRA-35 for Pyruvic Acid Relative to Excess Lactic Acid

TABLE 1

| Conc mole/liter | Feed Solution | Equilibrium Liquor | Resin | $K_d$ | Selectivity |
|---|---|---|---|---|---|
| Pyruvic Acid | 0.005 | 0.001 | 0.024 | 26.9115 | 14.69 |
| Lactic Acid | 0.503 | 0.386 | 0.706 | 1.832 | |
| Lactic Dimer | 0.006 | 0.003 | 0.019 | 6.715 | 3.67 |

A feed solution of 3 ml was prepared as shown in Table 1 containing lactic acid and pyruvic acid in water. The feed was 45.3 gram/liter lactic acid and 440 mg/liter pyruvic acid, representing a typical fermentation broth stream. This was contacted with a weak base anion resin, IRA-35, at 20 deg C., in a single stage batch equilibration experiment. A selectivity of 14.69 for pyruvic acid relative to lactic acid was observed. A total of 81.8% of the pyruvic acid was removed from the solution onto the ion exchange resin in this single stage batch experiment, whereas only 23.4% of the lactic acid was removed.

EXAMPLE 2

Purification of a Lactic Acid Feed Stream Comprising Trace Amounts of Pyruvic Acid and Oxalic Acid Using a Packed Column (Multistage) Contactor With Continuous Flow Three feed solutions were prepared to simulate fermentation broths comprising lactic acid. The first feed solution (FS1) was made combining 272.7 g 88% L-lactic acid (Pfansteihl), 2.572 g 95% pyruvic acid (Aldrich), 20.868 g 10% w/v oxalic acid (LabChem, Inc.), and deionized water to a volume of 4 liters. Similarly, a second feed solution (FS2) was prepared comprising 270.4 g 88% L-lactic acid, 2.424 g 95% pyruvic acid, 20.756 g 10% w/v oxalic acid, and deionized water in sufficient amount to attain a volume of four liters for the solution. A third feed solution (FS3) was prepared comprising 272.7 g 88% L-lactic acid, 2.4 g 95% pyruvic acid, 20.7 g 10% w/v oxalic acid, and deionized water in sufficient amount to attain a volume of four liters for the solution.

A 40 ml column was packed with Ionac A-365 weak base anion exchange resin (Sybron Chemicals, Inc.), a basic immiscible extractant. Ionac A-365 comprises porous polyacrylate gel bead structures, specifically comprising acrylic divinylbenzene, with polyamine functional groups. The resin packed in the column was washed with several bed volumes of deionized water. The packed column was capped off and placed on a ring stand in position for an upward flow of a feed stream.

An Eldex B-100-S-4 stainless steel reciprocating pump was used to adjust the rate at which water, feed solution, and treatment fluids were delivered to the column. The feed solutions, water and treatment fluids were run through the column at temperatures of between about 19° C. and 21° C. Four liters each of the lactic acid feeds FS 1 and FS2 and two and a half liters of FS3 were pumped in sequence through the column over a period of more than 52 hours. The solutions were fed, one after the other, to the bottom of the column and eluent was collected from the top of the column. Eluent fractions from the feed solutions were collected in the following order 6×30 ml, 2×120 ml, 29×240 ml, 1×40 ml, 8×240 ml, and 9×30 ml. The column was subsequently treated with an acidic solution and a basic solution, and thus 4×40 ml acidic eluent fractions, 2×40 ml deionized water wash fractions, 4×40 ml caustic (e.g. basic) eluent fractions, and 2×40 ml deionized water wash fractions were collected, as well.

Select eluent fractions were subsequently analyzed, undiluted, by HPLC. 100 μl of an eluent fraction was injected for each HPLC run at a flow rate of 1.4 ml per minute. All analyses were conducted at room temperature between 19° C. and 21° C. The mobile phase comprised 10% acetonitrile and 0.085% $H_3PO_4$ in deionized water. The HPLC column was a Jordi organic acid column 300 mm long and 7.8 mm in diameter. A UV detection device (210 nm) was used to detect compounds as they eluted from the HPLC column. The pH values of certain eluent fractions were determined.

Following collection of the fractions described above, two 30 ml samples were collected at a flow rate approximately half of the rate used for the previous fractions in order to determine if there were any kinetic limitations. Based on the data below, it appeared there were no kinetic effects.

Following the run of the feed stream, the column was regenerated. The column was washed with two bed volumes of deionized water, four bed volumes of 1 N HCl, followed by another wash comprising two bed volumes of deionized water. The column was next washed using four bed volumes of 1 N NaOH, followed by a wash of two bed volumes of deionized water. Feed solution runs and regeneration of the column can be described using the following chemical equations.

Feed Treatment:$R_3N \rightarrow R_3N$:Hlactic$\rightarrow R_3N$:HPyruvic-$R_3N$:HOxalic Regeneration(1):$R_3N$:HPyruvic and $R_3N$:HOxalic+HCl$\rightarrow$ $R_3N$:HCl+pyruvic acid and oxalic acid Regeneration(2):$R_3N$:HCl+NaOH$\rightarrow R_3N+H_2O$+NaCl A number of new peaks appeared in the acid and base elution fractions and the water washes that followed them. It is possible that some of these peaks could be explained by reactions between pyruvic acid and oxalic acid in the resin phase.

Initially the resin was in the form of $R_3N$. As the feed solution was fed onto the column, the immiscible basic extractant complexed with all of the acids present in the feed stream. As more of the feed solution was fed onto the column, the lactic acid that was complexed with the immiscible basic extractant was displaced by pyruvic acid. As more feed solution was fed onto the column, the pyruvic acid complexed with the immiscible basic extractant was displaced by oxalic acid. Analysis of HPLC traces of the eluent samples that were collected at the end of the flow of the feed solution over the column, reveals that oxalic acid was still being absorbed almost completely by the immiscible basic extractant at the end of the run. Breakthrough of pyruvic acid (pyruvic acid being displaced from the immiscible basic extractant) was considered to have occurred when pyruvic acid in an eluent sample had reached five percent of the gram/liter concentration in the feed. From the HPLC data, this happened at 192 bed volumes.

Other data collected from the run are summarized in the tables below.

TABLE 2

Sample peak areas of HPLC traces for the feed solutions

| | FS1 | FS2 | FS3 |
|---|---|---|---|
| Oxalic acid | 1614 | 1576 | 1614 |
| Pyruvic acid | 1462 | 1251 | 1292 |
| Lactic acid | 9503 | 7921 | 8285 |
| Lactic dimer | 3240 | 3544 | 3693 |
| Lactic trimer | 685 | 911 | 866 |

TABLE 3

Relevant $pK_a$ values for the acids involved

| ACID | $pK_a$ |
|---|---|
| HCL | −2 |
| OXALIC ACID | 1.27 |
| PYRUVIC ACID | 2.48 |
| FORMIC ACID | 3.75 |
| LACTIC ACID | 3.86 |
| ACETIC ACID | 4.76 |

TABLE 4

A comparison of an eluent sample and the feed it came from

| | FS1 | Eluent fraction (FS1 after run on column) |
|---|---|---|
| Oxalic acid | 512 | 0 |
| Pyruvic acid | 639 | 2 |
| Lactic acid | 44199 | 47288 |
| Lactic dimer | 15070 | 14179 |
| Lactic trimer | 3188 | 2676 |

The pyruvic acid area corresponds to a level of about 2 ppm or 0.002 gram/liter of pyruvic acid in the effluent.

Several impurities of unknown chemical composition that appeared in the HPLC traces of the feed solutions and eluent fractions are probably due to resin impurities such as residual monomer from the resin manufacturing and impurities present in the chemicals used to prepare the feed solution.

TABLE 5

The bed loading at breakthrough based on the theoretical bed capacity of 3.5 meq per ml

| Species | Method | Millimoles per milliliter of resin |
|---|---|---|
| Oxalic acid | from analytical data | 1.09 |
| Pyruvic acid | from analytical data | 1.27 |
| Lactic acid, Lactic dimer and Lactic trimer | from theoretical bed capacity | 1.14 |

EXAMPLE 3

Batchwise Treatment of Overhead Distillate From Lactic Acid Azeotropic Distillation A fermentation broth containing lactic acid had previously been purified by azeotropic distillation and other steps. This product contained 19 ppm pyruvic acid and 260.9 g/L lactic acid. 4.5 ml of this material was treated with about 1.2 ml of a weak base anion exchange resin, Sybron Ionac A-365, in the hydroxy form in a simple batch equilibrium adsorption. Approximately 38% of the lactic was removed. Remarkably, 90% of the pyruvic acid was removed leaving a product with less than 2 ppm pyruvic acid. A selectivity for pyruvic acid relative to lactic acid of 14.73 was estimated.

Additionally, an unknown acid "strong impurity" with an elution time of 7.27 minutes in this particular HPLC chromatographic analysis protocol was observed to be 99% removed by this treatment, with a selectivity of about 54.

In the table below, a chromatographic response factor for the unknown peak at 210 nanometer wavelength has been estimated based on refractive index data (not shown) suggesting that the species has a response factor 4 times greater than that of pyruvic acid.

TABLE 6

| Concentration mole/liter | Feed Solution | Equilibrium Liquor | Resin | $K_d$ | Selectivity | % Removal |
|---|---|---|---|---|---|---|
| Peak 7.27 | $12.57 \times 10^{-4}$ | $0.13 \times 10^{-4}$ | $52.47 \times 10^{-4}$ | 401.21 | 176.51 | 99% |
| Pyruvic Acid | $0.22 \times 10^{-4}$ | $0.02 \times 10^{-4}$ | $0.73 \times 10^{-4}$ | 33.49 | 14.73 | 90% |
| Lactic Acid | $2899.92 \times 10^{-4}$ | $1805.11 \times 10^{-4}$ | $4102.98 \times 10^{-4}$ | 2.27 | | 38% |
| Lactic Dimer | $91.26 \times 10^{-4}$ | $0.55 \times 10^{-4}$ | $178.90 \times 10^{-4}$ | 4.11 | 1.81 | 52% |

After treatments, the product was found to contain very low levels of pyruvic acid, less than found in samples of lactic acid supplied by ADM and Pfanstiehl.

TABLE 7

All concentrations in ppm except for lactic acid, in gram/liter

| Acid Species | Impurity Type | Feed | Effluent 1 | Effluent 2 | Effluent 3 | Effluent 4 |
|---|---|---|---|---|---|---|
| Lactic acid | Product | 60.76 gram/L | 40.28 gram/L | 62.64 gram/L | 63.16 gram/L | 62.92 gram/L |
| Pyruvic acid | Strong | 270 | <20 | <20 | <20 | <20 |
| HCL | Strong | 117 | <20 | <20 | <20 | <20 |
| $H_2SO_4$ | Strong | 125 | <20 | <20 | <20 | <20 |
| $H_3PO_4$ | Strong | 690 | <20 | <20 | <20 | <20 |
| Malic acid | Weak | 32 | 19 | 39 | 26 | 23 |
| Acetic acid | Weak | 15 | <10 | 12 | 14 | 15 |
| Succinic acid | Weak | 48 | <20 | 41 | 33 | 30 |

EXAMPLE 4

Continuous Treatment of Overhead Distillate from Lactic Acid Azeotropic Distillation A fermentation broth containing lactic acid had previously been purified by azeotropic distillation and other steps.

This product did not contain detectable levels of pyruvic acid, 743 g/L lactic acid, and an estimated 0.22 gram/liter of the unknown peak at 7.27 minutes.

A sample of 10.0 ml of this material was treated with about 2.4 ml of a weak base anion exchange resin, Sybron Ionac A-365, in the hydroxy form in a continuous column contacting mode.

Approximately 15% of the lactic was removed. Remarkably, 98% of the unknown strong impurity was removed, giving a lactic acid product of less than 4 ppm of this strong impurity.

This example teaches the effectiveness of the current invention for removing strong impurities whose exact identity is unknown.

EXAMPLE 5

Continuous Treatment of Low pH Fermentation Broths

Two low pH lactic acid fermentation broths were prepared (each was about 5.5 liters in volume) and combined. The low pH broth was treated with SAC (strongly acid cation exchange) resin (>0.1 moles of resin/mole lactic acid) and WBA (weakly basic anion exchange) resin (~0.03 moles resin/mole lactic acid). The SAC resin was packed in two 37 mm×450 mm columns, each 480 ml, operated in tandem and the WBA resin was in a two 15 mm×300 mm columns, of 53 ml each, in tandem.

We see from the tabulated data that both inorganic and organic acids can be strong impurities can be removed with good effectiveness despite the high level of lactic acid. A flowrate of 1.4 BV/hour for the SAC and 6 BV/hour for the WBA was used.

EXAMPLE 6

Continuous Treatment of 11 Liters of Fermentation Broth

The resins used in example 5 were regenerated and the treatment was repeated with a fresh batch of fermentation material. A typical effluent fraction collected during the run, was 62.8 gram/liter lactic acid and 12.4 ppm pyruvic acid.

EXAMPLE 7

Continuous Treatment of 11 Liters of Fermentation Broth

The resins used in example 6 were regenerated and the treatment was repeated with a fresh batch of fermentation material. Two fractions were collected. After ion exchange treatment, each fraction was concentrated by evaporation to nearly 28% w/w lactic acid. Prior to evaporation, the concentrations are as shown in Table 8.

TABLE 8

| Gram/liter concentrations | Feed | Fraction |
|---|---|---|
| Pyruvic Acid | 0.145 | 0.005 |
| Lactic Acid | 62.000 | 62.000 |
| Malic Acid, Peak 9.00 | 0.130 | 0.030 |

It can be seen that the pyruvic acid level is lowered from 145 mg/liter to 0.5 mg/liter. This remarkable reduction in pyruvic acid level of nearly 300-fold was achieved with only minor loss of lactic acid.

The anion resin was regenerated and it was found that 0.64% of the total feed mass of lactic acid had been adsorbed on the ion exchange resin with the pyruvic acid. In this case, the strong acids $H_2SO_4$ and $H_3PO_4$ are present in the feed and also act as displacing acids Additional displacing acids can be used to regenerate the resin and selectively displace the additional lactic acid in preference to the pyruvic acid.

The anion ion exchange resin was regenerated and found that the ratio of M lactic acid to M pyruvic acid on the resin was 19.34. This is as expected due to the selectivity limit of the resin. This load cannot be exceeded.

EXAMPLE 8

Comparison of Liquid Immiscible Amine and Solid Amine Ion Exchanger for Sequence of Strong Impurities A acid mixture solution was prepared with 52.78 g/L lactic acid 0.2 to 0.3 g/L each the acid impurities listed in the table.

An 8 ml aliquot of the acid mixture was equilibrated with 1.0 ml of Sybron Ionac A-365 weak base anion resin and the selectivities measured relative to lactic acid.

An separate aliquot of 5 ml of the acid mixture was separately equilibrated with 5 ml of extractant Y, consisting of 1.0 molar trilaurylamine and 1.0 molar dodecanol, with dodecane as the diluent.

TABLE 9

| Species | Selectivity of Ionac A-365 for impurity relative to lactic acid | Selectivity of Extractant 'Y' for impurity relative to lactic acid |
|---|---|---|
| Pyruvic Acid | 20.99 | |
| L-Malic Acid | 198.8 | 3.32 |
| Formic Acid | 4.01 | 3.06 |
| Acetic Acid | 0.169 | 0.42 |
| Propionic Acid | 0.101 | 1.42 |
| n-butyric acid | 0.100 | 5.74 |
| Iso-butyric acid | 0.072 | 6.53 |

EXAMPLE 9

U38 Strong Base Anion Resin to Selectively Remove Strong Impurities Followed by Displacement with Displacing Acid Amberlite IRA-93 strong base anion resin was prepared in a 62 ml column and regenerated to give the hydroxide form. The resin was used to treat an excess of concentrated lactic acid fermentation broth that had previously already been treated with a cation and weak base anion resin.

The resin was displaced using 1 N $H_2SO_4$. Five fractions were collected. The first two fractions contained significant weak impurities, acetic acid and formic acid, as well as lactic acid. The latter fractions contained significant pyruvic acid as well as some lactic acid.

EXAMPLE 10

Calculations of the Effect of Varying Pyruvic Acid Levels in the Feed on Removal and Displacement Effectiveness The feed solution had a ratio of lactic acid moles to pyruvic acid moles of 117:1. After treatment with an amine immiscible basic extractant, the product had a comparable ratio of 486:1. Thus, the lactic acid had been purified by selective removal of the pyruvic acid. The extract contained 5.6% mole of the lactic acid that was present in the feed, and this diminished the yield.

In general, more stages or a longer extraction sequences could not improve this situation very much. This was because the feed already had quite low levels of pyruvic acid impurity, yet the amine only had a limited selectivity for pyruvic acid over lactic acid of 18-fold.

The values used for the distribution coefficient for each of the species into the amine phase were assumed to be constant. This was reasonable as concentrations do not change significantly over the course of the extraction. The distribution coefficients for each species were assumed to be independent, which is also reasonable as the amine was only lightly loaded in this case. At low loadings, the amine extract complex was probably dominated by the formation of 1:1 complexes of pyruvic acid with the amine. The energy of these complexes and the distribution was roughly correlated with the $pK_a$ of the acid. The amine used here was probably not highly enhanced. For this example, it was assumed that the $K_d$ for pyruvic acid into the amine phase, was the ratio of pyruvic acid mole/liter of acid free amine phase to pyruvic acid mole/liter of acid free water phase. The distribution coefficient for pyruvic acid was assumed to be 5.0 and that for lactic acid to be 0.278, giving a selectivity of 18.0.

TABLE 10

Effect of feed concentration of pyruvic acid when the same lactic acid concentration (0.66 M) is used.

| | | | | | |
|---|---|---|---|---|---|
| Pyruvic acid concentration initially in feed | 1000 | 500 | 300 | 100 | ppm |
| Volume of immiscible basic extractant required | 10.66 | 10.57 | 10.53 | 10.49 | liter |
| Bed volume treated | 93.84 | 94.64 | 94.96 | 95.29 | liter |
| Lactic acid losses to extract | 3.9% | 4.7% | 5.1% | 5.4% | |
| $Y_{pyruvic}$, ratio M pyruvic acid to M lactic acid on the ion exchange bed | 30.5% | 15.4% | 9.2% | 3.1% | |

Effective pyruvic acid level in the effluent is very low after a second bed volume, due to the large number of stages in ion exchange. A level of 2 ppm pyruvic acid was observed in practice. Assuming that the bed had a selectivity of 18:1 for pyruvic over lactic acid, then during regeneration it was possible to separate the lactic acid from the pyruvic acid nearly quantitatively in all cases where the ion load fraction on the bed, $y_{pyruvic}$, was greater than 100/18=5.56% w/w. If the loading was less than this, then a subsequent additional ion exchange treatment would be required for that effluent. The example above is for the case of full desorption of all the species on the ion exchanger without fractionation of the eluents, which is desirable.

EXAMPLE 11

The Calculations of Example 10 are Repeated, But the Lactic Acid Concentration Is Varied

TABLE 11

Effect of varying concentration of lactic acid concentration in feeds having the same pyruvic acid concentration.

| | | | | |
|---|---|---|---|---|
| Pyruvic acid concentration initially in feed | 500 | 500 | 500 | ppm |
| Volume of immiscible basic extractant required | 10.57 | 12.79 | 15.96 | liter |
| Bed volume treated | 94.64 | 78.19 | 62.64 | liter |
| Lactic acid losses to extract | 4.74% | 4.88% | 5.02% | |
| $Y_{pyruvic}$ | 15.4% | 12.7% | 10.2% | |
| Lactic acid concentration initially in feed | 0.66 | 0.80 | 1.00 | mol/L |

For a given level of pyruvic acid, as the lactic acid concentration increases, the fractional loading of lactic acid on the bed decreased. This makes obtaining separate fractions of lactic acid and pyruvic acid more difficult. The preceding description of specific embodiments of the present invention is not intended to be a complete list of every possible embodiment of the invention. Persons skilled in this field will recognize that modifications can be made to the specific embodiments described here that would be within the scope of the present invention.

What is claimed is:

1. A process for purifying an organic acid, comprising:
   providing an aqueous feed stream comprising a product organic acid and at least one strong contaminant, wherein the molar concentration of the product organic acid is at least 20 times greater than the molar concentration of the strong contaminant;
   contacting the aqueous feed stream with a first immiscible basic extractant that has a selectivity for the strong contaminant relative to the product organic acid that is greater than about 3, whereby the majority of the strong contaminant and less than about 33 wt % of the product organic acid become complexed with the first immiscible basic extractant;
   separating the complexed first immiscible basic extractant from the aqueous stream, thereby producing a first effluent stream that comprises product organic acid and that has a greater ratio of product organic acid to strong contaminant than the aqueous feed stream did; and
   contacting the complexed first immiscible basic extractant with a displacing acid, wherein the first immiscible basic extractant has a greater affinity for the displacing acid than it does for the strong contaminant or the product organic acid, and wherein the displacing acid is present in sufficient amount to cause product organic acid to be selectively displaced from the complexed first immiscible basic extractant, thereby, over time, producing a second effluent stream that comprises a major amount of product organic acid and displacing strong contaminant from the complexed first immiscible basic extractant, thereby following production of the second effluent stream with the production of a third effluent stream that comprises a major amount of strong contaminant and that is separated from the second effluent stream;
   wherein the total amount of product organic acid present in the first effluent stream and in the second effluent stream is at least about 900/0 by weight of the product organic acid that was present in the feed stream.

2. The process of claim 1, wherein the total amount of product organic acid present in the first effluent stream and in the second effluent stream is at least about 98% by weight of the product organic acid that was present in the feed stream.

3. The process of claim 1, wherein the molar concentration of the product organic acid is at least 90 times greater than the molar concentration of the strong contaminant.

4. The process of claim 1, wherein the molar concentration of the product organic acid is at least 500 times greater than the molar concentration of the strong contaminant.

5. The process of claim 1, wherein the molar concentration of the product organic acid is at least 1000 times greater than the molar concentration of the strong contaminant.

6. The process of claim 1, wherein the selectivity is at least about 15.

7. The process of claim 1, wherein the selectivity is at least about 25.

8. The process of claim 1, wherein the selectivity is at least about 100.

9. The process of claim 1, wherein the strong contaminant is an organic acid that has a $pK_a$ that is lower than that of the product organic acid.

10. The process of claim 1, wherein the product organic acid is lactic acid.

11. The process of claim 10, wherein the strong contaminant has a $pK_a$ less than about 3.46.

12. The process of claim 10, wherein the strong contaminant is selected from the group consisting of pyruvic acid, oxalic acid, citraconic acid, citric acid, and mixtures thereof.

13. The process of claim 10, wherein the selectivity is greater than about 25.

14. The process of claim 10, wherein the molar concentration of the lactic acid in the feed stream is at least 300 times greater than the molar concentration of the strong contaminant in the feed stream, and the selectivity is greater than about 500.

15. The process of claim 1, wherein the first immiscible basic extractant comprises a weak base ion exchange resin.

16. The process of claim 1, wherein the displacing acid is selected from the group consisting of HCl, $H_2SO_4$, $H_3PO_4$, oxalic acid, and trifluoroacetic acid.

17. The process of claim 1, wherein the feed stream, the first effluent stream, and the second effluent stream further comprise a weak contaminant, the process further comprising:
   combining the first effluent stream and the second effluent stream to form a combined product organic acid stream;
   contacting the combined product organic acid stream with a second immiscible basic extractant, whereby the majority of the product organic acid becomes complexed with the second immiscible basic extractant; and
   separating the complexed second immiscible basic extractant from the stream, thereby producing a fourth effluent stream that comprises the majority of the weak contaminant that was present in the combined product organic acid stream.

18. The process of claim 17, further comprising:
   contacting the fourth effluent stream with a third immiscible basic extractant that has a greater affinity for the product organic acid than for the weak contaminant, whereby the majority of the product organic acid that is present in the fourth effluent stream becomes complexed with the third immiscible basic extractant;
   separating the complexed third immiscible basic extractant from the stream, thereby producing a fifth effluent that comprises the majority of the weak contaminant that was present in the combined product organic acid stream;

contacting the complexed second immiscible basic extractant and the complexed third immiscible basic extractant with one or more displacing acids, thereby displacing product organic acid therefrom in one or more additional effluent streams.

19. The process of claim 17, wherein the second immiscible basic extractant comprises a weak base ion exchange resin comprising a tertiary amine moiety.

20. The process of claim 17, wherein the product organic acid is lactic acid and the weak contaminant is an organic acid having a $pK_a$ greater than about 4.26.

21. The process of claim 20, wherein the weak contaminant is an organic acid selected from the group consisting of propionic acid, butyric acid, malonic acid, succinic acid, and mixtures thereof.

22. The process of claim 1, further comprising:

contacting the third effluent stream with an additional immiscible basic extractant that has a greater affinity for the strong contaminant than for the product organic acid, whereby the majority of the strong contaminant present in the third effluent stream becomes complexed with the additional immiscible basic extractant;

separating the complexed additional immiscible basic extractant from the remaining stream, thereby producing an additional effluent that comprises the majority of the product organic acid that was present in the third effluent.

23. The process of claim 1, wherein the feed stream comprises a fermentation broth.

24. The process of claim 1, wherein the first immiscible basic extractant comprises a solid basic extractant, contacting the aqueous feed stream with the first immiscible basic extractant is performed in a packed bed, and the ratio of molar concentration of product organic acid to molar concentration of strong contaminant in the second effluent stream is within about 10% of the selectivity.

25. The process of claim 1, wherein the first immiscible basic extractant comprises a liquid basic extractant, contacting the aqueous feed stream with the first immiscible basic extractant is performed as a multistage process, and the ratio of product organic acid to strong contaminant is within about 10% of the selectivity.

26. The process of claim 1, wherein the aqueous feed stream comprises more than one strong contaminant, and wherein at least one of the strong contaminants is a displacing acid.

27. The process of claim 1, wherein the feed stream and the first effluent stream further comprise a weak contaminant, the process further comprising:

processing the first effluent stream by at least one of extraction or distillation, whereby at least two fractions are produced, a purified product organic acid fraction comprising between about 90% and 99.5% by weight of the product organic acid that was present in the feed stream, and a weak contaminant fraction comprising product organic acid and weak contaminant, wherein the ratio of molar concentration of product organic acid to molar concentration of weak contaminant in the weak contaminant fraction is less than the ratio of molar concentration of product organic acid to molar concentration of weak contaminant in the feed stream;

contacting the weak contaminant fraction with a third immiscible basic extractant that has a selectivity for the product organic acid relative to the weak contaminant that is greater than about 3, whereby the majority of the product organic acid and less than about 33 wt % of the weak contaminant become complexed with the third immiscible basic extractant;

separating the complexed third immiscible basic extractant from the aqueous stream, thereby producing an effluent stream that comprises weak contaminant and that has a greater ratio of weak contaminant to product organic acid than the aqueous feed stream did; and contacting the complexed third immiscible basic extractant with a displacing acid, wherein the third immiscible basic extractant has a greater affinity for the displacing acid than it does for the product organic acid or the weak contaminant, and wherein the displacing acid is present in sufficient amount to cause product organic acid and weak contaminant to be displaced over a period of time from the complexed third immiscible basic extractant, thereby producing a weak contaminant effluent stream that comprises a major amount of weak contaminant and a product organic acid stream that comprises a major amount of the product organic acid.

28. The process of claim 27, wherein the purified product organic acid fraction comprises between about 95% by weight and 99.5% by weight of the product organic acid that was present in the feed stream.

29. The process of claim 1, wherein the first immiscible basic extractant has previously been used to treat a solution comprising the product organic acid and at least one weak contaminant.

30. A process for purifying lactic acid, comprising:

providing an aqueous feed stream comprising lactic acid and at least one strong contaminant acid having a $pK_a$ less than about 3.46, wherein the molar concentration of lactic acid is at least 20 times greater than the molar concentration of the strong contaminant acid;

contacting the aqueous feed stream with a first basic ion exchanger that has a greater affinity for the strong contaminant acid than for lactic acid, whereby the majority of the strong contaminant acid and some lactic acid become complexed with the first basic ion exchanger;

separating the complexed first basic ion exchanger from the aqueous stream, thereby producing a first effluent strewn that comprises lactic acid and that has a greater ratio of lactic acid to strong contaminant acid than the aqueous feed stream did; and contacting the complexed first basic ion exchanger with a displacing acid, wherein the first basic ion exchanger has a greater affinity for the displacing acid than it does for the strong contaminant acid or lactic acid, whereby lactic acid is selectively displaced from the complexed first basic ion exchanger, thereby, over time, producing a second effluent stream that comprises a major amount of lactic acid and displacing strong contaminant from the complexed first basic ion exchanger, thereby following production of the second effluent stream with the production of a third effluent stream that comprises a major amount of strong contaminant acid and that is separated from the second effluent stream;

wherein the total amount of lactic acid present in the first effluent stream and the second effluent stream is at least about 90% by weight of the lactic acid that was present in the feed stream.

31. The process of claim 30, wherein the molar concentration of lactic acid is at least 90 times greater than the molar concentration of the strong contaminant acid in the aqueous feed stream.

32. The process of claim 30, wherein the molar concentration of lactic acid is at least 500 times greater than the molar concentration of the strong contaminant acid in the aqueous feed stream.

33. The process of claim 30, wherein the molar concentration of lactic acid is at least 1000 times greater than the molar concentration of the strong contaminant acid in the aqueous feed stream.

34. The process of claim 30, wherein the strong contaminant acid is selected from the group consisting of pyruvic acid, oxalic acid, citraconic acid, citric acid, and mixtures thereof.

35. The process of claim 30, wherein the molar concentration of lactic acid in the feed stream is at least 100 times greater than the molar concentration of the strong contaminant acid in the feed stream, and the selectivity is greater than about 250.

36. The process of claim 35, wherein the molar concentration of the product organic acid in the feed stream is at least 300 times greater than the molar concentration of the strong contaminant acid in the feed stream, and the selectivity is greater than about 500.

37. The process of claim 30, wherein the first basic ion exchanger comprises a weak base ion exchange resin.

38. The process of claim 30, wherein the first basic ion exchanger has an affinity for the displacing acid that is at least 10 times greater than its affinity for pyruvic acid.

39. The process of claim 30, wherein the displacing acid is selected from the group consisting of HCl, $H_2SO_4$, and $H_3PO_4$.

40. The process of claim 30, wherein the feed stream, the first effluent stream, and the second effluent stream further comprise a weak contaminant organic acid having a $pK_a$ greater than about 4.26, and the process further comprises:
combining the first effluent stream and the second effluent stream to form a combined lactic acid stream;
contacting the combined lactic acid stream with a second basic ion exchanger, whereby the majority of the lactic acid becomes complexed with the second basic ion exchanger; and
separating the complexed second basic ion exchanger from the stream, thereby producing a fourth effluent stream that comprises the majority of the weak contaminant that was present in the combined lactic acid stream.

41. The process of claim 40, further comprising:
contacting the fourth effluent stream with a third basic ion exchanger that has a greater affinity for lactic acid than for the weak contaminant acid, whereby the majority of the lactic acid that is present in the fourth effluent stream becomes complexed with the third basic ion exchanger;
separating the complexed third basic ion exchanger from the stream, thereby producing a fifth effluent that comprises the majority of the weak contaminant acid that was present in the combined lactic acid stream;
contacting the complexed second basic ion exchanger and the complexed third basic ion exchanger with one or more displacing acids, thereby displacing lactic acid therefrom in one or more additional effluent streams.

42. The process of claim 40, wherein the second immiscible basic extractant comprises a weak base or strong base ion exchange resin.

43. The process of claim 40, wherein the weak contaminant is an organic acid selected from the group consisting of propionic acid, butyric acid, malonic acid, succinic acid, and mixtures thereof.

44. The process of claim 30, further comprising:
contacting the third effluent stream with an additional basic ion exchanger that has a greater affinity for the strong contaminant acid than for lactic acid, whereby the majority of the strong contaminant acid present in the third effluent stream becomes complexed with the additional basic ion exchanger;
separating the complexed additional basic ion exchanger from the stream, thereby producing an additional effluent that comprises the majority of the lactic acid that was present in the third effluent.

45. The process of claim 30, wherein the first effluent stream and the second effluent stream collectively have a ratio of molar concentration of lactic acid to molar concentration of strong contaminant that is greater than 300.

46. The process of claim 45, wherein the first effluent stream and the second effluent stream collectively have a ratio of molar concentration of lactic acid to molar concentration of strong contaminant that is greater than about 1,000.

47. The process of claim 30, wherein at least 98% by weight of the lactic acid present in the feed stream is recovered in the first effluent stream and the second effluent stream.

48. The process of claim 30, wherein the aqueous feed stream comprises or is obtained from a fermentation broth.

49. The process of claim 48, wherein the aqueous feed stream comprises no more than about 0.15 moles of cations selected from the group consisting of Ca, Mg, Na, Fe, Zn, Zr, and Li, per mole of lactic acid; no more than about 0.05 moles of anions selected from the group consisting of Cl, $SO_4$, $PO_4$, and $NO_3$, per mole of lactic acid; nor more than about 0.03 mole of strong acid contaminants selected from the group consisting of pyruvic acid, oxalic acid, citraconic acid, and citric acid, per mole of lactic acid; and no more than about 0.02 mole of weak acid contaminants selected from the group consisting of propionic acid, butyric acid, malonic acid, and succinic acid, per mole of lactic acid.

50. A process for purifying lactic acid, comprising:
providing an aqueous fermentation broth comprising lactic acid and pyruvic acid, wherein the molar concentration of the lactic acid is at least 20 times greater than the molar concentration of pyruvic acid;
removing cells from the broth to form an aqueous feed stream;
contacting the aqueous feed stream with means for complexing pyruvic acid, the means having a greater affinity for pyruvic acid than for lactic acid, whereby the majority of the pyruvic acid and some lactic acid form complexes therewith;
separating the complexes from the aqueous stream, thereby producing a first effluent stream that comprises lactic acid and that has a greater ratio of lactic acid to pyruvic acid than the aqueous feed steam did; and
contacting the complexes with means for displacing lactic acid and pyruvic acid therefrom wherein the lactic acid is selectively displaced from the complexes thereby, over time, producing a second effluent stream that comprises a major amount of lactic acid and displacing pyruvic acid from the complexes, thereby following production of the second effluent stream with the production of a third effluent stream that comprises a major amount of pyruvic acid and that is separated from the second effluent stream;
wherein the total amount of lactic acid present in the first effluent stream and the second effluent stream is at least about 98% by weight of the lactic acid that was present in the feed stream.

51. A process for purifying an organic acid, comprising:

providing an aqueous feed stream comprising a product organic acid and at least one strong contaminant, wherein the molar concentration of the product organic acid is at least 20 times greater than the molar concentration of the strong contaminant;

contacting the aqueous feed stream with a first immiscible basic extractant that has a selectivity for the strong contaminant relative to the product organic acid that is greater than about 3, whereby the majority of the strong contaminant and less than about 33 wt % of the product organic acid become complexed with the first immiscible basic extractant;

separating the complexed first immiscible basic extractant from the aqueous stream, thereby producing a first effluent stream that comprises product organic acid and that has a greater ratio of product organic acid to strong contaminant than the aqueous feed stream did; and exposing the complexed first immiscible basic extractant to at least one of (1) a change in temperature, (2) a change in solvent concentration, or (3) a change in displacing agent concentration, wherein exposure causes product organic acid to be selectively displaced from the complexed first immiscible basic extractant, thereby over a period of time producing a second effluent stream that comprises a major amount of product organic acid and displacing strong contaminant from the complexed first immiscible basic extractant, thereby following production of the second effluent stream with the production of a third effluent stream that comprises a major amount of strong contaminant and that is separated from the second effluent stream;

wherein the total amount of product organic acid present in the first effluent stream and in the second effluent stream is at least about 90% by weight of the product organic acid that was present in the feed stream.

* * * * *

UNITED STATES PATENT AND TRADEMARK OFFICE
CERTIFICATE OF CORRECTION

PATENT NO. : 6,641,734 B2
DATED : November 4, 2003
INVENTOR(S) : Cockrem et al.

It is certified that error appears in the above-identified patent and that said Letters Patent is hereby corrected as shown below:

Column 20,
Line 1, please delete "900/0" and insert -- 90% -- therefor.

Column 24,
Line 55, please delete "therefrom wherein" and insert -- therefrom, wherein -- therefor.

Signed and Sealed this

Thirteenth Day of April, 2004

JON W. DUDAS
*Acting Director of the United States Patent and Trademark Office*